(12) United States Patent
Petrini et al.

(10) Patent No.: US 6,773,729 B2
(45) Date of Patent: Aug. 10, 2004

(54) COMBINATION OF GINSENG AND GINKGO TO IMPROVE COGNITIVE SKILLS

(75) Inventors: Orlando Petrini, Comano (CH); Andrew Scholey, Newcastle upon Tyne (GB)

(73) Assignee: Pharmaton S.A., Bioggio (CH)

( * ) Notice: Subject to any disclaimer, the term of this patent is extended or adjusted under 35 U.S.C. 154(b) by 0 days.

(21) Appl. No.: 10/286,161

(22) Filed: Nov. 1, 2002

(65) Prior Publication Data

US 2003/0064118 A1 Apr. 3, 2003

Related U.S. Application Data

(63) Continuation of application No. 09/740,493, filed on Dec. 18, 2000.
(60) Provisional application No. 60/172,500, filed on Dec. 17, 1999, and provisional application No. 60/208,357, filed on May 31, 2000.

(51) Int. Cl.$^7$ .......................... A61K 35/78; A61K 31/70
(52) U.S. Cl. ....................... 424/725; 424/728; 424/752; 514/23
(58) Field of Search ................................ 424/725, 752, 424/728; 514/23

(56) References Cited

U.S. PATENT DOCUMENTS 6,083,932 A * 7/2000 Pang et al. .................... 514/54

OTHER PUBLICATIONS

Scholey et al., "Acute dose–dependent cognitive effects of Ginkgo biloba, Panax Ginseng and their combination in healthy young volunteers: differential interactions with cognitive demand", Hum Psychopharmacol, Jan., 2002, 17(1):35–44, abstract.*

Kennedy et al., "Modulation of cognition and mood following administration of single doses of Ginkgo biloba, ginseng and and ginkgo/ginseng combination to healthy young adults", Physiol Behav. Apr. 15, 2002, 75(5):739–51, abstract.*

Kennedy et al., "Differential, does dependent changes in cognitive performance following acute administration of a Ginkgo biloba/Panax ginseng combination to healthy young volunteers", Nutr Neurosci, 2001 4(5):399–412, abstract.*

Wesnes et al., "The cognitive, subjective, and physical effects of a ginkgo biloba/panax ginseng combination in healthy volunteers with neurasthenic complaints", Psychopharmacol Bull, 1997, 33(4):677–83.*

Kennedy et al., "The dose dependent cognitive effects of acute administration of Ginkgo biloba to healthy young volunteers", Psychopharmacology, Sep. 2000, 151:416–423.*

Petkov Vesselin D. et al: Memory Effects of Standardized Extracts of Panax ginseng (G115), Ginkgo biloba (GK 501) and their Combination Fincosan (PHL–00701) Planta Med. 1993, 59(2):106–114.

Kennedy David O. et al: "Glucose administration, heart rate and cognitive performance:effects of increasing mental effort" Psychopharmacology 2000 149:63–71.

Petkov V D et al: "Effects of standardized extracts GK501, from Ginkgo Biloba L., G115 from panax ginseng C.A. Meyer, and their combination, gincosan(PHL–00701), on the brain levels of biogenic Monoamines and on the serum content of prolactin, growth hormone and ACTH" Phytotherapy Research, 1993, 7(2):139–145.

Belcheva S et al "Gingko biloba L. and Panax ginseng C.A. Mey. as memory–enhancing and anti–anxiety drugs." Dokladi na Blgarskata Akademiya na Naukite. 1994. 47(2):121–124.

Wesnes K A et al "The cognitive, subjective, and physical effects of a Ginkgo biloba/Panax ginseng combination in healthy volunteers with neurasthenic complaints." Psycopharmacology Bulletin, 1997, 33(4):677–683.

Wesnes K A et al "The memory enhancing effects of a Ginkgo biloba/Panax ginseng combination in healthy middle–aged volunteers." Psychopharmacology, 2000, 152(4):353–361.

* cited by examiner

Primary Examiner—Leon B. Lankford, Jr.
Assistant Examiner—Ruth A. Davis
(74) Attorney, Agent, or Firm—Robert P. Raymond; Susan K. Pocchiari; Mary-Ellen M. Devlin

(57) ABSTRACT

A dietary supplement consisting essentially of a combination of Ginseng and Ginkgo to improve the speed of memory and memory quality in normal, healthy subjects and to prevent deterioration of the speed of memory in people with decreased cognitive functions, and to counteract cognitive fatigue.

3 Claims, 3 Drawing Sheets

COMBINATION OF GINSENG AND GINKGO TO IMPROVE COGNITIVE SKILLS

RELATED APPLICATIONS

This application is a continuation of U.S. application Ser. No. 09/740,493, filed Dec. 18, 2000, ABN which claims, as does the present application, priority benefit to U.S. Provisional Application serial Nos. 60/172,500, filed Dec. 17, 1999 and 60/208,357, filed May 31, 2000, the disclosures of all of which are incorporated by reference in their entirety.

FIELD OF THE INVENTION

The present invention relates to a novel use of a combination of the plants Ginseng, more precisely *Panax ginseng*, and Ginkgo, more precisely *Ginkgo biloba* and/or the combination of extracts of both plants to improve cognitive skills. The combination is useful for improving the speed of memory and memory quality in normal, healthy subjects as well as to prevent deterioration of the speed of memory in people with decreased cognitive functions as well as to counteract cognitive fatigue.

BACKGROUND OF THE INVENTION

Extracts of *Ginkgo biloba* contain ginkgo-flavone glycosides and terpenoids which are known to have vaso-regulating and blood viscosity decreasing properties. The main indications for which Ginkgo is prescribed in Western countries, such as France and Germany, are intermittent claudication and cerebral insufficiency.

The roots of *Panax ginseng* C. A. Meyer contain several triterpene glycosides named ginsenosides (or panaxosides) which are believed to contribute to the adaptogenic and physical performance enhancing properties of the ginseng extracts. It is used to treat anemia, diabetes mellitus, insomnia, neurasthenia, gastritis, abnormal blood pressure, dyspepsia, overstrain and fatigue.

Petkov et al. disclose that the standardized extracts of *Panax ginseng, Ginkgo biloba* and a combination thereof improve the learned behavior of young and old rodents (Petkov, V. D. et al., Planta Med. 59 (1993) pp. 106–114). This study showed that the combination of *Panax ginseng* and *Ginkgo biloba* did not exhibit a synergistic effect compared with the single active principles in rats.

It has previously been suggested (Moss and Scholey, Psychopharmacology, 1996 124(3):255–60, Kennedy and Scholey, Psychopharmacology, 2000 149(1):63–71) that some demanding cognitive tasks may be facilitated by the simple augmentation of delivery of metabolic substrates to the brain. As an example, a previous study from this laboratory (Kennedy and Scholey Psychopharmacology, 2000 149(1):63–71) investigated the relationship between heart rate, blood glucose levels and performance on a "demanding" mental arithmetic task (serial verbal subtraction of 7 from a given number between 800 and 1000; "serial 7s"), a "less demanding" mental arithmetic task (serial subtraction of 3; "serial 3s"), and a long term verbal memory task. It was found that not only did both serial subtraction tasks engender significant increases in heart rate above that engendered by somatically identical counting tasks, but that performance on both was also related to the magnitude of fall in blood glucose levels during task performance. Performance on the most demanding task (serial 7s) was also not only improved by a glucose drink, but was also related to resting heart rate.

SUMMARY OF THE INVENTION

Unexpectedly, it was found in cognitive tests that administering a combination of extracts of the root of *Panax ginseng* C. A. Meyer and of the leaves of *Ginkgo biloba* to humans positively effects cognitive skills, for example, such as the speed and quality of memory in normal, healthy subjects. Both *Panax ginseng* and *Ginkgo biloba* have been extensively used for various indications in Chinese medicine and are described in the traditional Chinese Pharmacopoeia. Ginkgo extracts and Ginseng extracts are known to have effects on cognitive functions, yet the effects produced by the combination are of a novel type.

Therefore the present invention is directed to a method to enhance the speed of memory and memory quality in normal, healthy subjects comprising the administration of a medication and/or a dietary supplement containing a combination of Ginseng and Ginkgo. Further, the combination may be used to prevent deterioration of the speed of memory in people with decreased cognitive functions and to counteract cognitive fatigue. Specifically, the composition of the present invention consists of herbal ingredients, for example, derived by an extraction from Ginseng roots and Ginkgo leaves. Another aspect of the present invention is a method for the enhancement of the mental effort and/or cognitive performance, in particular of children or young adults, said method comprising co-administration of synergistically enhancing amounts of the plant *Panax ginseng*, extracts thereof and/or the principle active substances thereof and the plant *Ginkgo biloba*, extracts thereof and/or the principle active substances thereof to a person in acute need of such treatment.

The Ginseng extract contains among other substances ginsenosides and polysaccharides, while the Ginkgo extract contains among other substances ginkgo flavone glycosides and terpene lactones. While all these substances are known to have pharmacological activities, the range of their pharmacological actions has not yet been fully elucidated, but in vitro studies indicate that some of them have antioxidant properties and that they inhibit platelet aggregation, while others exert an action on the oxygen uptake in the cells and others again may exert an immunomodulating action. It is considered, however, that only complete extracts prepared according to the methods set out in this invention possess the activities necessary to achieve the effects related to this invention.

It is a primary object of the present invention to provide a method to improve the speed of memory and memory quality in normal, healthy subjects, to prevent deterioration of the speed of memory in people with decreased cognitive functions and to counteract cognitive fatigue. It is a further object of the present invention to provide a method for improving the speed of memory and to prevent a decrease of the speed of memory by taking formulations comprising herbal ingredients, wherein the medication and/or the dietary supplement is manufactured pursuant to a controlled process that preserves the herbal curing qualities of the ingredients. It is still a further object of the present invention to provide a method for improving the speed of memory and to prevent a decrease of the speed of memory comprising herbal ingredients and having minimal or no side effects and thus being safe for internal consumption.

DETAILED DESCRIPTION OF THE INVENTION

Figure 1A:
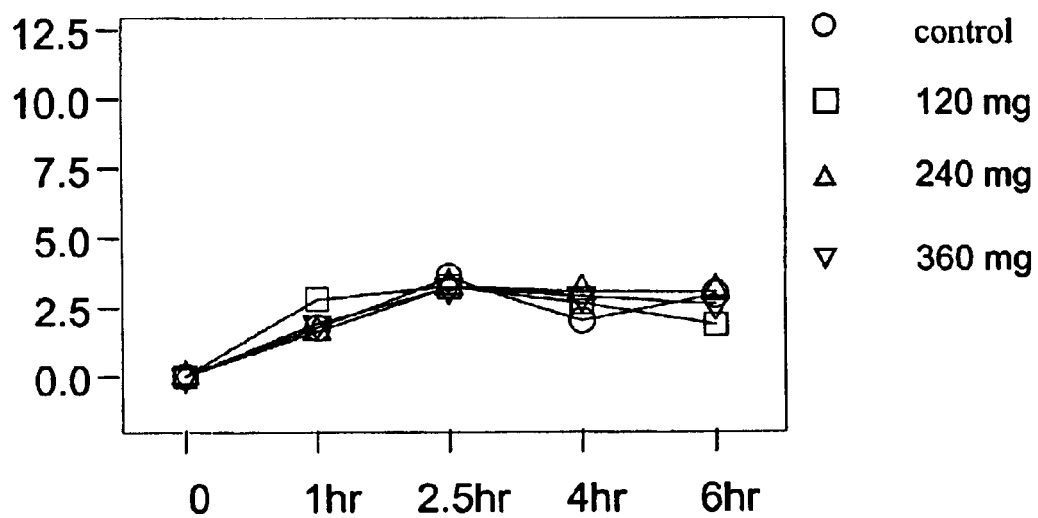
FIGS. 1a and 1b show the number of responses and errors in the Serial Sevens test of subjects who have taken *Ginkgo biloba*.

The invention relates to a method to improve the speed of memory and memory quality in normal, healthy subjects as well as to prevent deterioration of the speed of memory in people with decreased cognitive functions as well as to counteract cognitive fatigue by co-administration of or a combination-administration of:

(i) the plant *Panax ginseng*, extracts thereof and/or the principal active substances thereof, and
(ii) the plant *Ginkgo biloba*, extracts thereof and/or the principal active substances thereof.

In this context under the term "co-administration" is meant that each of the two components (i) and (ii) as described above are administered separately but within a close timely relationship. The two components (i) and (ii) are taken within a break of about 12 hours or less. Preferably, both of them are taken within 4 hours, more preferably within one hour and most preferably together.

Under the term "combination-administration" is meant that both components (i) and (ii) are present in one formulation.

The two components (i) and (ii) may be formulated independently of each other or together in one formulation. For example, the formulation may comprise dried Ginseng roots or Ginkgo leaves or other plant components, that optionally are powdered, the formulation may be in the form of tablets, coated tablets, powders, powders in capsules, syrups, solutions or suspensions, for example, on the basis of water, ethanol or a mixture thereof, dragees, gels, injections or any other suitable manner well known to the skilled person. Preferred are oral administration forms.

Under the term "plant" is understood the plant itself as well as plant parts comprising the active ingredients, for example, the leaves, the stems, the fruits or roots as mentioned above. Preferably, the plant or plant components are dried. Optionally, they may be powdered.

Under the term "extracts" is meant that the plants or plant components are extracted with a suitable solvent like water, ethanol, a mixture thereof, oils or any other suitable solvent well known in the state of the art of extracting plants. These extracts can be used as such if pharmacologically acceptable or the solvent of the resulting solutions is removed and the residue is used as such or after further work up, for example, after resolving or re-suspending in a pharmacologically suitable solvent.

Under the terms "principal active ingredients" and "principal active substances" are meant all active ingredients that are mainly responsible for the pharmacological effect. Preferably, the formulation comprises all those ingredients of the plant of interest that are responsible for at least 75 percent, more preferably at least 90 percent of the pharmacological effect. These active ingredients may be won from the plants or synthesized chemically.

A preferred embodiment concerns a method according to the above prescribed in that Ginseng extract is used containing, among other substances, ginsenosides and polysaccharides, preferably containing at least 3%, more preferably 3.5 to 5.0%, most preferably 3.6 to 4.4% ginsenosides and Ginkgo extract is used containing, among other substances, ginkgo flavone glycosides and terpene lactones, preferably containing at least 20%, more preferably 21.0 to 30%, most preferably 22.0 to 27.0% ginkgo flavone glycosides and 2 to 10%, preferably 4 to 8%, more preferably 5.0 to 7.0%, most preferably about 6% terpene lactones.

Another aspect of the invention concerns a method for the enhancement of mental effort and/or cognitive performance comprising co-administration of synergistically enhancing amounts of:

(i) the plant *Panax ginseng*, extracts thereof and/or the principal active substances thereof, and
(ii) the plant *Ginkgo biloba*, extracts thereof and/or the principal active substances thereof,
to a person in acute need of such treatment.

Preferably, the method comprises co-administration of 200 to 1200 mg of a composition comprising:

(i) about 100 parts per weight of an extract of the plant *Panax ginseng*, and
(ii) about 60 parts per weight of an extract of the plant *Ginkgo biloba*, wherein said composition is administered to a person 0.5 to 6.0 hours, preferably 0.45 to 5.5 hours, before said person is in need of such treatment. Preferably, the method comprises administration of 300 to 1000 mg, more preferably 300 to 990 mg, most preferably 320, 640 or 960 mg of a composition comprising 100 mg *Panax ginseng* extract, preferably Ginseng extract G115 and 60 mg *Ginkgo biloba* extract, preferably Ginkgo extract GK501, a composition which is commercially available from Pharmaton S. A., Switzerland as PHL-00701 or under the tradename GINCOSAN®.

The term "dietary supplement" as used hereinabove and hereinbelow includes a composition comprising components (i) and (ii), which may be used without prescription by a third party, for example, a physician. The components may be taken together with meals or separated thereof, on a daily basis or only sometimes. The components may be formulated as described above for example.

Preferably the medication and/or dietary supplement comprises (i) Ginseng extract that contains at least 4% ginsenosides and
(ii) and Ginkgo extract containing at least 24% ginkgo flavone glycosides and 6% terpene lactones.

Preferably, the medication and/or dietary supplement is administrated in a form suitable for oral administration, such as granules, tablets, capsules, drops, syrups or others. Dietary supplements are most preferred.

EXAMPLES

In a pilot study the influence of a combination of *Panax ginseng* and *Ginkgo biloba* on cognitive skills was conducted, whereby cognitive testing was included as one of the primary outcome variables. In this study, the effects of the combination were evaluated in a three-month, double blind, placebo controlled, parallel group, tolerability and efficacy trial. Sixty-four normal volunteers (aged 40 to 65) were selected for the study on the basis of fulfilling the ICD-10 F48.0 criteria for neurasthenia. They were randomly assigned to four equal dosing groups, receiving either placebo or 80, 160 or 320 mg b.i.d. of the combination for three months. A range of assessments was performed on the day prior to dosing, and again at days 1, 30 and 90. Each day the assessments were performed twice; once 60 minutes after the morning dose, and again 5 hours later (60 minutes after the afternoon dose). Three primary outcome variables were defined in the study protocol. The first was the combined accuracy score on a number of computerized memory tests. The second was the number of correct responses on a stress indicator, and the third the heart rate at maximum exercise load on a cycle ergometer. Other assessments from these assessment systems were defined as secondary variables. All volunteers completed the study, the treatments were well tolerated, and no serious adverse events were observed. At the pre-defined primary endpoint (day 90 at 1 hour post morning dosing), dose related improvements were seen on the memory tests, and a significant benefit on the ergometry assessment of heart rate at maximum load. This trial satisfied the pre-defined criteria for concluding that the combination was effective. The positive effects did not appear to be related to the degree of neurasthenia with which the volunteers presented, from which it can be assumed the compound would work in a broader population. Certainly this pilot study gave evidence of enhancements to cognitive function, which vindicated the incorporation of cognitive testing. Nonetheless, some important issues were unresolved.

In order to verify the effectiveness, safety and tolerability of the medication and/or dietary supplement of the present invention, a randomized, placebo-controlled, double-blind parallel-group study was conducted in a large and representative sample of normal, healthy subjects. This study was carried out in accordance with the Declaration of Helsinki and the Principles of Good Clinical Practice. The results are set forth below:

Objective—To definitively identify the cognition enhancing effects of the combination of Ginseng and Ginkgo, to compare two dosing regimens (160 mg b.i.d vs. 320 mg o.d.), and to explore the time profile of these effects.

Design—A double-blind, placebo-controlled, randomized, parallel group, 16 week repeated assessment trial in normal middle-aged volunteers.

Patients—Male and female volunteers randomized, aged between 39–65 completed the trial.

Intervention—The trial product, or its placebo counterpart, was given to healthy middle aged volunteers (either 160 mg b.i.d or 320 mg o.d.) for a period of twelve weeks (Visits 4–7). This was preceded by a four week run-in of placebo and followed up by a two week wash out. Volunteers underwent cognitive testing at the following time points: pre-dose, and 1, 3 and 6 hours post dose at each four weekly visit. The volunteers completed a total of four training sessions over Visits 1 and 2. At each visit the volunteers also completed a number of questionnaires to assess quality of life. At each visit, vital signs were assessed in the morning and afternoon and any adverse events were recorded. Changes to concomitant medications were recorded throughout the study. At the penultimate visit, a blood sample was taken again from each volunteer.

Outcome Measures—Primary outcome measure: baseline-adjusted changes in memory tests at the end of the trial. Secondary outcome measures: baseline-adjusted changes in memory tests at intermediate time points and quality of life questionnaires.

Results—The five factors identified: speed of memory processes, quality of episodic secondary memory, power of attention, continuity of attention and quality of working memory, reflected five very important aspects of everyday function. The primary variable was a quality of working and secondary memory score, formed by combining the scores which contributed to the quality of working memory factor and the quality of secondary memory factor. This score has previously been shown to be sensitive to the influence of the combination. The combination significantly improved the memory index at 1 and 6 hours post-dosing, though at 1 hour post dosing it was only the split daily dosing schedule which was superior to placebo. The Speed Factor also supported these data, the volunteers became faster as well as more accurate. The most consistent effects were seen towards the end of the study days, suggesting that the compound helps to counteract cognitive fatigue. The combination did not, however, increase self-rated alertness, suggesting that the action of the compound is not of the "stimulant" type, but instead more of a facilitator of endurance and the ability to sustain quality. The safety and tolerability of the compound were excellent. Overall, the compound enhances the quality of both working and secondary memory in the healthy middle aged which, considering its excellent safety and tolerability, makes it a highly attractive product for this population.

Conclusion—The combination can produce clinically important improvements to the quality of memory function in healthy middle aged adults. These effects occur after four weeks of dosing and are sustained throughout the entire 14 week study period. Taken together with the excellent safety and tolerability of the product, these findings make the combination a highly attractive product for healthy subjects. The effects produced by the combination are readily distinguishable from those produced by Ginkgo or Ginseng extracts alone and represent a novel way of improving cognitive functions in normal, healthy subjects. This effect can be expected in subjects with decreased cognitive functions as well.

To prevent the decrease of speed of memory or to improve speed of memory and to counteract cognitive fatigue, the medication and/or dietary supplement should be taken in dosages corresponding to 160 and 700 mg of extract, preferably 320 mg daily. The total amount of extract may be divided up in 1 to 2 portions a day. The daily dose should be taken in two doses, preferably in the morning and at lunch time.

Impressive improvement of the memory speed and reduction of cognitive fatigue can be expected within 4 weeks of continuous use. The optimum effect is maintained or amplified on longer use.

Serial Sevens

In order to verify the synergistic effect of the medication and/or dietary supplement of the present invention, a modified computerized version of the Serial Sevens test was utilized. The original Serial Sevens test (M. Hayman, Arch. Neurol. Psychiatry 17: 125–130 (1947)) has appeared in a number of forms, including as part of the Mini-Mental State Examination (L. A. Taylor et al., J. Behav. Med. 11: 279–291 (1985)). In the current study's novel computerized version, participants were presented with a number from which they were instructed to serially subtract in sevens, entering their three digit responses on the keyboard number pad. In the present study the test was 2 minutes in duration. A standard instruction screen informed the participant to count backwards in sevens from the given number, as quickly and accurately as possible, using the return key to enter each response. Participants were also instructed verbally that if they were to make a mistake they should carry on subtracting from the new incorrect number. Starting numbers between 800 and 999 were randomly generated, and were presented on the screen only until the first response had been made, after which time individual entered digits were represented by asterisks. The task was scored as total number of subtractions. The number of incorrect responses was also recorded. In the case of an error, subsequent responses were scored as positive if they were correct in relation to the new number.

This study was carried out in accordance with the Declaration of Helsinki and the Principles of Good Clinical Practice. The results are set forth below:

Design—Randomized, double-blind, balanced crossover, placebo+3 potentially effective doses, 7 day wash-out.

Patients—Male and female healthy volunteers randomized, aged between 20–22 completed the trial.

Treatments—On each study day participants received six capsules of identical appearance, each containing:
  (i) Ginkgo: 60 mg of *Ginkgo biloba* extract (GK 501, Pharmaton Switzerland) standardized to a content of 24% ginkgo flavone glycosides and 6% terpene lactones or an inert placebo. Depending on the condition to which they were allocated on that particular day the combination corresponded to a dose of either 0 (placebo), 120, 240, or 360 mg of *Ginkgo biloba* extract.
  (ii) Ginseng: 100 mg of Ginseng extract (G115, Pharmaton Switzerland), standardized to contain 4% ginsenosides, or an inert placebo. Depending on the condition to which they were allocated on that particular day the combination corresponded to a dose of either 0 (placebo), 200, 400, or 600 mg of Ginseng extract.
  (iii) Gincosan®: A combination of 60 mg of standardized *Ginkgo biloba* extract (GK 501, Pharmaton Switzerland) and 100 mg of standardized Ginseng extract (G115, Pharmaton Switzerland), which is commercially available from Pharmaton Switzerland as Gincosan®, or an inert placebo. Depending on the condition to which they were allocated on that particular day, the combination corresponded to a dose of either 0 (placebo), 320, 640, or 960 mg of the combined extracts.

Procedures—Each participant was required to attend a total of five study days that were conducted seven days apart to ensure an appropriate wash-out between conditions. Testing for the whole cohort took place on two days of the week, with two separate testing schedules on each day (five participants per session) commencing either between 9 and 9:30am or between 9:30 and 10 am. Testing took place in a suite of laboratories with participants visually isolated from each other.

On arrival at their first session on the first day, participants were randomly allocated to a treatment regime using a Latin square which counterbalanced the order of treatments across the four active days of the study.

The first day of the study was identical to the following four, but no treatment (active or placebo) was offered, to allow familiarization with the tasks and procedure and control for practice effects. Data from the first day were not included in the analysis Each study day comprised five identical testing sessions. The first was a pre-dose testing session which established baseline performance for that day, and was immediately followed by the day's treatment (days 2 to 5). Further testing sessions took place between 1 and 1.5 hours, 2.5 and 3 hours, 4 and 4.5 hours and 6 and 6.5 hours following consumption of the day's treatment.

Each testing session comprised completion of the two 2 minute computerized serial subtraction tasks.

Results—Each 'total subtractions' and 'number of errors' score from the four post-dose testing sessions was transformed to a 'change from baseline' score by subtracting the corresponding baseline score.

(i) Ginkgo

The data obtained in this test are shown in Table I

TABLE I

|  | Dose rate | Pre-dose | | 1 to 1.5 hour | | 2.5 to 3 hours | | 4 to 4.5 hours | | 6 to 6.5 hours | |
| --- | --- | --- | --- | --- | --- | --- | --- | --- | --- | --- | --- |
| Serial 7s Total Subtractions | 360 mg | 29.55 | 3.14 | 31.45 | 3.10 | 32.75 | 3.07 | 32.45 | 2.86 | 32.15 | 2.53 |
|  | 240 mg | 30.7 | 3.15 | 32.3 | 2.86 | 33.95 | 2.95 | 33.75 | 2.85 | 33.75 | 2.82 |
|  | 120 mg | 29.1 | 2.02 | 31.9 | 1.99 | 32.35 | 1.91 | 31.75 | 1.91 | 30.95 | 2.01 |
|  | placebo | 29.05 | 2.10 | 30.8 | 2.87 | 32.6 | 2.70 | 31.05 | 2.15 | 32 | 2.28 |
| Serial 7s Errors | 360 mg | 2.65 | 0.59 | 2.5 | 0.37 | 2.3 | 0.36 | 2.05 | 0.40 | 2.85 | 0.60 |
|  | 240 mg | 2.2 | 0.53 | 2.1 | 0.50 | 1.85 | 0.42 | 1.35 | 0.33 | 2.45 | 0.44 |
|  | 120 mg | 2.5 | 0.47 | 1.9 | 0.40 | 2.05 | 0.39 | 2.35 | 0.56 | 1.85 | 0.54 |
|  | placebo | 2.35 | 0.46 | 2.35 | 0.48 | 3.1 | 0.81 | 2.05 | 0.52 | 1.8 | 0.48 |

Planned comparisons of the change from baseline data revealed that, whilst there were no significant improvements in the total number of subtractions for any of the doses of Ginkgo, there was a significant improvement in the number of errors in comparison to placebo for all doses at the 2.5 to 3 hour time point (120 mg [t(171)=2.16, p<0.05], 240 mg [t(171)=1.98, p<0.05] and 360 mg [t(171)=1.98, p<0.05]).

Figure 1B:
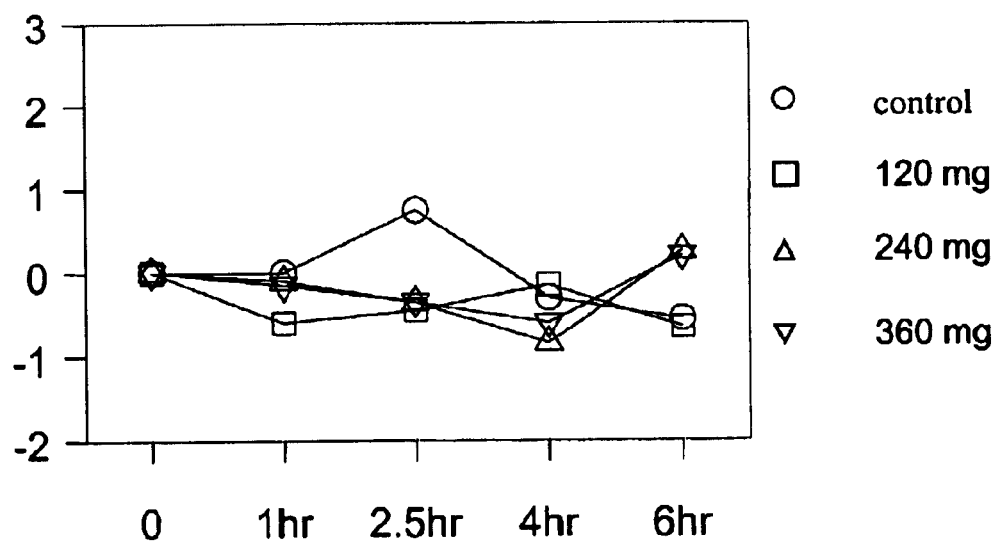

Mean performance data (raw and change from baseline scores) are represented in FIGS. 1*a* and 1*b*.

(ii) Ginseng

The data obtained in this test are shown in Table II

TABLE II

|  | Dose rate | Pre-dose | | 1 to 1.5 hour | | 2.5 to 3 hours | | 4 to 4.5 hours | | 6 to 6.5 hours | |
| --- | --- | --- | --- | --- | --- | --- | --- | --- | --- | --- | --- |
| Serial 7s Total Subtractions | 600 mg | 36.05 | 3.18 | 39.6 | 3.43 | 40.5 | 3.77 | 39.7 | 3.38 | 39.15 | 3.26 |
|  | 400 mg | 35.8 | 3.18 | 38.15 | 3.12 | 40.1 | 3.09 | 39.3 | 3.05 | 40.2 | 3.01 |
|  | 200 mg | 35.2 | 2.62 | 37 | 2.45 | 38 | 2.56 | 36.95 | 2.52 | 37.5 | 2.53 |
|  | placebo | 34.85 | 2.34 | 38.65 | 2.8 | 39.6 | 3.08 | 37.9 | 3.07 | 39.65 | 2.6 |
| Serial 7s Errors | 600 mg | 1.5 | 0.33 | 1.65 | 0.57 | 1.65 | 0.5 | 1.5 | 0.41 | 2.4 | 0.31 |
|  | 400 mg | 1.95 | 0.49 | 2.05 | 0.53 | 1.95 | 0.46 | 1.1 | 0.28 | 1.2 | 0.31 |
|  | 200 mg | 1.9 | 0.37 | 2 | 0.51 | 1.2 | 0.32 | 1.25 | 0.41 | 1.55 | 0.5 |
|  | placebo | 1.35 | 0.28 | 2.25 | 0.41 | 1.4 | 0.33 | 1.6 | 0.33 | 1.55 | 0.37 |

Planned comparisons of the change from baseline data revealed that there was a significant decrement in performance for the 200 mg dose of Ginseng with participants making fewer subtractions than following placebo at the 1 to 1.5 hour session [t(171)=2.07, p<0.05], 2.5 to 3 hour session [t(171)=2.01, p<0.05] and the 6 to 6.5 hour session [t(171)=2.59, p<0.05].

However, there was a significant improvement in accuracy following the 400 mg dose of Ginseng with a reduction in errors, in comparison to placebo, at the 4 to 4.5 hour session [t(171)=2.46, p<0.05], and the 6 to 6.5 hour session [t(171)=2.12, p<0.05], with a similar improvement for the 200 mg dose at the 4 to 4.5 hour time point [t(171)=2.01, p<0.05].

Figure 2A:
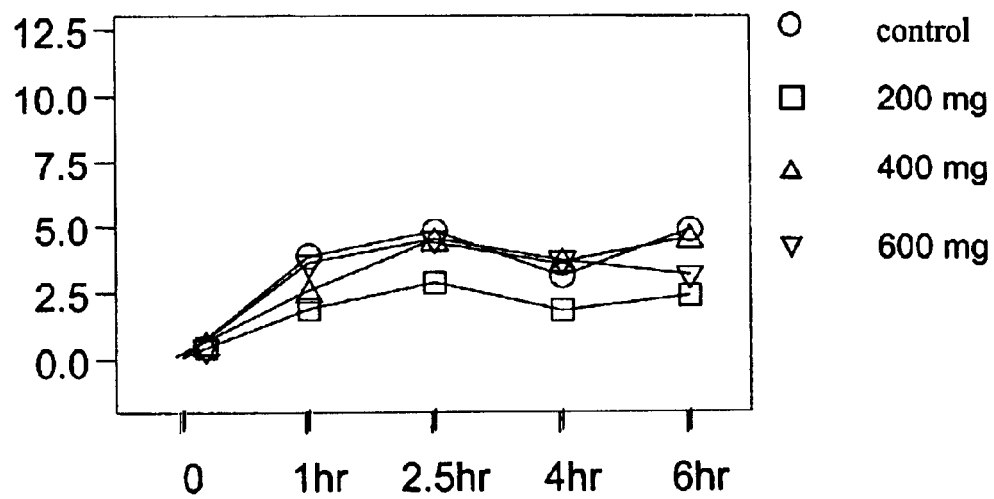
FIGS. 2a and 2b show the number of responses and errors in the Serial Sevens test of subjects who have taken Ginseng.
Figure 2B:
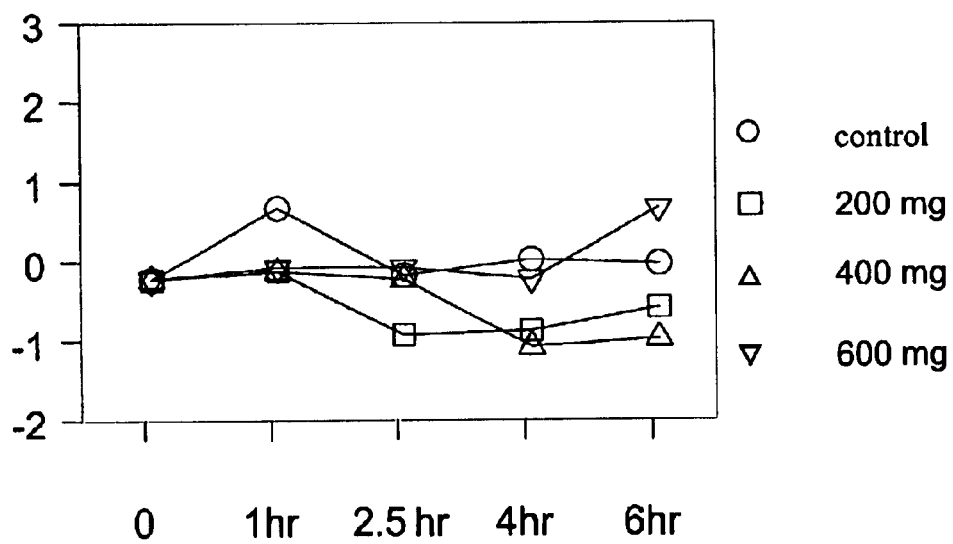

Mean performance data (raw and change from baseline scores) for both tasks are represented in FIGS. 2*a* and 2*b*.

(iii) Ginkgo and Ginseng (Gincosan®)

The data obtained in this test are shown in Table III

TABLE III

|  | Dose rate | Pre-dose | | 1 to 1.5 hour | | 2.5 to 3 hours | | 4 to 4.5 hours | | 6 to 6.5 hours | |
| --- | --- | --- | --- | --- | --- | --- | --- | --- | --- | --- | --- |
| Serial 7s Total Subtractions | 960 mg | 38.75 | 4.25 | 39.3 | 3.94 | 39.45 | 3.87 | 40.75 | 3.88 | 40.1 | 4.00 |
|  | 640 mg | 38.45 | 3.30 | 40.85 | 3.36 | 41.95 | 3.44 | 43.25 | 4.00 | 42.35 | 3.79 |
|  | 320 mg | 37.85 | 3.39 | 42.45 | 3.59 | 43.25 | 3.45 | 43 | 3.39 | 43.4 | 3.77 |
|  | placebo | 39.8 | 3.32 | 39.75 | 3.89 | 40.65 | 3.39 | 40.65 | 3.60 | 41.4 | 3.52 |
| Serial 7s Errors | 960 mg | 2.6 | 0.53 | 2.9 | 0.52 | 2.1 | 0.64 | 2.25 | 0.58 | 2.85 | 0.60 |
|  | 640 mg | 3.4 | 0.54 | 3.2 | 0.65 | 2.8 | 0.62 | 2.2 | 0.68 | 2.95 | 0.68 |
|  | 320 mg | 2.95 | 0.53 | 3.8 | 0.75 | 3.35 | 0.86 | 3.9 | 0.71 | 3.5 | 0.78 |
|  | placebo | 2.3 | 0.76 | 2.4 | 0.43 | 4.35 | 1.79 | 3.15 | 0.63 | 4.35 | 1.15 |

Planned comparisons of the change from baseline data revealed that participants made more subtractions in comparison to placebo at all time points following the 320 mg dose of the combination (1 to 1.5 hours [t(171)=3.42, p<0.001], 2.5 to 3 hours [t(171)=3.36, p<0.001], 4 to 4.5 hours [t(171)=3.17, p<0.01] and 6 to 6.5 hours [t(171)=2.91, p<0.01]). Participants also made more subtractions at the 4 to 4.5 hour session following ingestion of 640 mg of the combination [t(171)=2.91, p<0.01].

There were also marked improvements in accuracy for all doses of the combination at both the 2.5 to 3 hours session (320 mg [t(171)=2.22, p<0.05], 640 mg [t(171)=3.46, p<0.001], 960 mg [t(171)=3.43, p<0.001]) and the 6 to 6.5 hours session (320 mg [t(171)=2.02, p<0.05], 640 mg [t(171)=3.36, p<0.001], 960 mg [t(171)=2.42, p<0.05], with a single significant reduction at the 4 to 4.5 hours session following the 640 mg dose [t(171)=2.75, p<0.01].

Figure 3A:
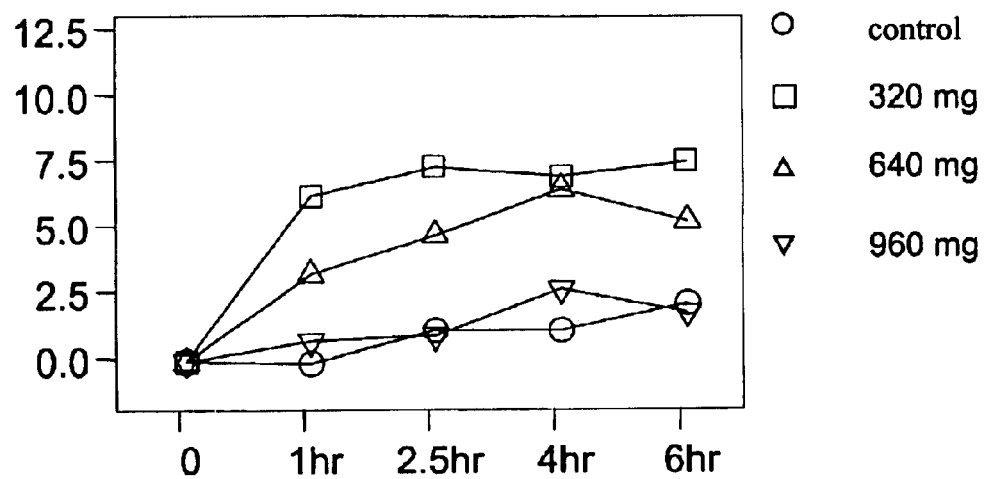
FIGS. 3a and 3b show the number of responses and errors in the Serial Sevens test of subjects who have taken a combination of *Ginkgo biloba* and Ginseng.
Figure 3B:
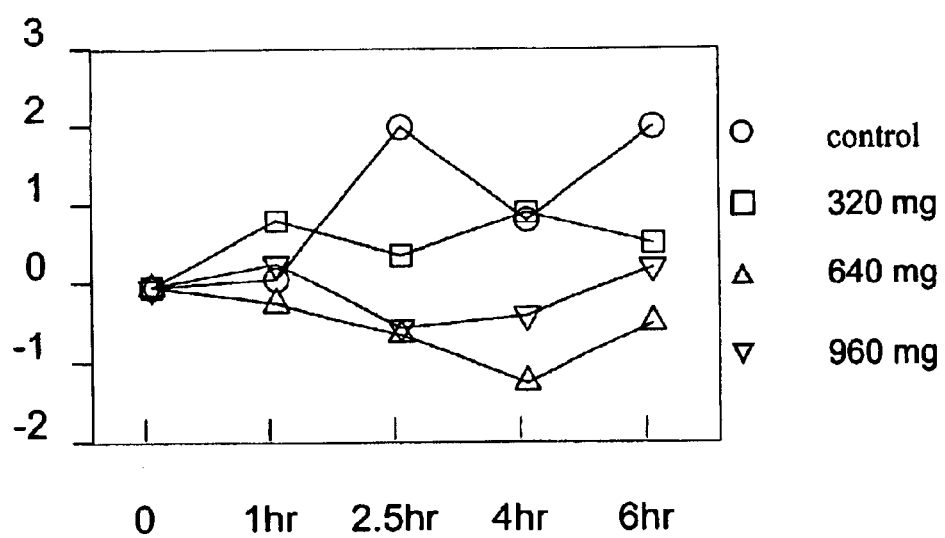

Mean performance data (raw and change from baseline scores) for both tasks are represented in FIGS. 3*a* and 3*b*.

Conclusion—A pattern of results was evinced on the Serial Sevens task. In this case the 320 mg dose was associated with increased speed of performance at all time points, with a similar profile of improvements that attained significance at a single time point (4 to 4.5 hours), for the 640 mg dose. All three doses were associated with significantly improved accuracy of performance, with this effect most marked for the 640 mg dose.

It would appear that these comprehensive improvements in performance for all doses of the combination product represent the working of a synergism between the two component extracts.

It will be readily apparent to those skilled in the art that various changes and modifications of an obvious nature may be made without departing from the spirit of the invention, and all such changes and modifications are considered to fall within the scope of the appended claims. While the composition of the present invention has been set forth in what is believed to be preferred embodiments, it is recognized that departures may be made within the spirit and scope of the following claims.

All publications cited herein are incorporated by reference in their entireties.

What is claimed is:

1. A method for the enhancement of the cognitive performance of a healthy child or a young adult comprising oral administration of 200 to 1000 mg of a composition comprising:
   (i) 100 parts per weight of an extract of the plant *Panax ginseng* containing at least 3% ginsenosides; and
   (ii) 60 parts per weight of an extract of the plant *Ginkgo biloba* containing at least 20% ginkgo flavone glycosides and 2 to 10% terpene lactones,
wherein said composition is administered 0.5 to 6.0 hours before said child or young adult is in need of such a treatment.

2. The method according to claim 1 wherein:
   (i) the extract of the plant *Panax ginseng* contains 3.5 to 5.0% ginsenosides; and
   (ii) the extract of the plant *Ginkgo biloba* contains 21.0 to 30% ginkgo flavone glycosides and 4 to 8% terpene lactones.

3. The method according to claim 2 wherein:
   (i) the extract of the plant *Panax ginseng* contains 3.6 to 4.4% ginsenosides; and
   (ii) the extract of the plant *Ginkgo biloba* contains 22.0 to 27.0% ginkgo flavone glycosides and 5.0 to 7.0% terpene lactones.

* * * * *